(12) United States Patent
Hadvary et al.

(10) Patent No.: US 10,117,989 B2
(45) Date of Patent: Nov. 6, 2018

(54) SYRINGE TYPE PUMP

(71) Applicant: PharmaSens AG, Biel-Benken (CH)

(72) Inventors: Pual Hadvary, Biel-Benken (CH);
Hansjorg Tschirky, Sissach (CH)

(73) Assignee: PharmaSens AG, Biel-Benken (CH)

( * ) Notice: Subject to any disclaimer, the term of this patent is extended or adjusted under 35 U.S.C. 154(b) by 0 days.

(21) Appl. No.: 14/738,995

(22) Filed: Jun. 15, 2015

(65) Prior Publication Data

US 2015/0273139 A1 Oct. 1, 2015

Related U.S. Application Data

(62) Division of application No. 13/878,569, filed as application No. PCT/EP2011/067535 on Oct. 7, 2011.

(51) Int. Cl.
| | |
|---|---|
| *A61M 5/142* | (2006.01) |
| *A61M 5/145* | (2006.01) |
| *A61M 5/172* | (2006.01) |
| *A61B 5/15* | (2006.01) |
| *A61M 5/32* | (2006.01) |
| *A61B 5/00* | (2006.01) |
| *A61B 5/145* | (2006.01) |
| *A61M 5/31* | (2006.01) |
| *A61M 5/315* | (2006.01) |

(52) U.S. Cl.
CPC ....... *A61M 5/14216* (2013.01); *A61B 5/0004* (2013.01); *A61B 5/145* (2013.01); *A61B 5/150229* (2013.01); *A61B 5/4839* (2013.01); *A61M 5/1452* (2013.01); *A61M 5/1454* (2013.01); *A61M 5/14248* (2013.01); *A61M 5/1723* (2013.01); *A61M 5/3287* (2013.01); *A61M 5/3129* (2013.01); *A61M 2005/14252* (2013.01); *A61M 2005/31518* (2013.01); *A61M 2205/50* (2013.01)

(58) Field of Classification Search
CPC .. A61B 10/007; A61B 10/0045; A61B 5/1405
USPC .......................................................... 600/573
See application file for complete search history.

(56) References Cited

U.S. PATENT DOCUMENTS

| | | |
|---|---|---|
| 3,472,627 A | 10/1969 | Jiri |
| 4,525,164 A | 6/1985 | Loeb et al. |
| 4,781,688 A | 11/1988 | Thoma et al. |
| 5,931,814 A | 8/1999 | Alex et al. |

(Continued)

FOREIGN PATENT DOCUMENTS

| | | |
|---|---|---|
| WO | WO 98/01173 A1 | 1/1998 |
| WO | WO 02/15965 A2 | 2/2002 |

(Continued)

*Primary Examiner* — Daniel Cerioni
(74) *Attorney, Agent, or Firm* — Xsensus, LLP

(57) ABSTRACT

The subcutaneous injection device contains a pump and a mechanism for inserting a cannula into the patient's skin. The cannula is fixedly positioned relative to the pump and the insertion mechanism has a flexible surface adhering to the skin. The flexible surface is positioned relative to the cannula in such a way that in a first position the tip of the cannula is concealed by the surface and in a second position the cannula is exposed beyond the surface. The insertion mechanism brings the surface from the first to the second position, thereby pulling the skin against the tip of the cannula.

9 Claims, 3 Drawing Sheets

(56) References Cited

U.S. PATENT DOCUMENTS

| | | | |
|---|---|---|---|
| 6,692,456 B1 * | 2/2004 | Eppstein | A61B 10/0045 600/309 |
| 2002/0022855 A1 * | 2/2002 | Bobroff | A61M 5/158 606/185 |
| 2006/0264894 A1 * | 11/2006 | Moberg | A61M 5/1413 604/503 |
| 2008/0026486 A1 * | 1/2008 | Cooper | C08B 5/02 436/518 |
| 2008/0051697 A1 * | 2/2008 | Mounce | A61M 5/1413 604/32 |

FOREIGN PATENT DOCUMENTS

| | | |
|---|---|---|
| WO | WO 02/28455 A1 | 4/2002 |
| WO | WO 2007/141210 A1 | 12/2007 |
| WO | WO 2008/024812 A2 | 2/2008 |
| WO | WO 2008/080990 A1 | 7/2008 |
| WO | WO 2009/016636 A2 | 2/2009 |
| WO | WO 2010/080715 A1 | 7/2010 |

\* cited by examiner

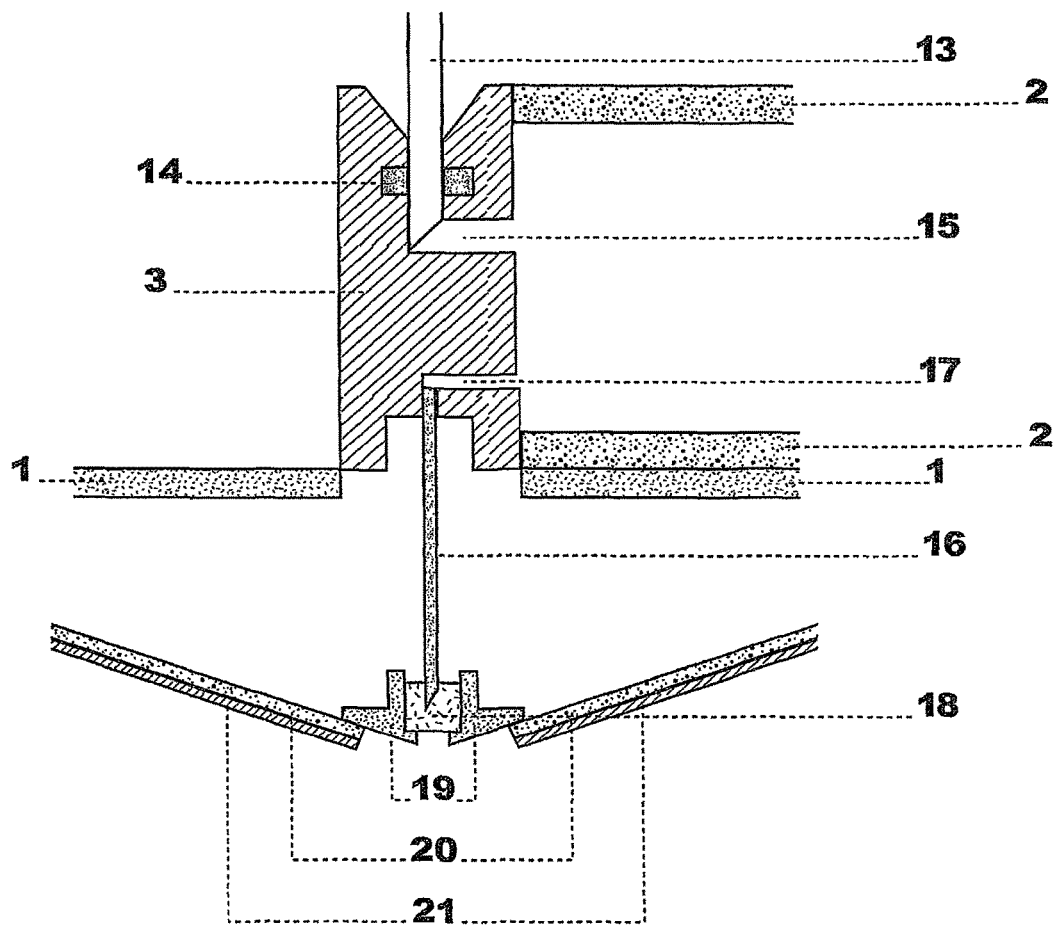

SYRINGE TYPE PUMP

RELATED APPLICATIONS

This a Divisional application of co-pending U.S. patent application Ser. No. 13/878,596 filed Oct. 7, 2011, and claims the benefit of that application and PCT/EP2011/067535 filed Oct. 7, 2011 and European Patent Application No. 10187141.6 filed Oct. 11, 2010.

FIELD OF THE INVENTION

The present invention is related with a syringe type pump according to the preamble of claim 1.

BACKGROUND

One major field of application for this type of pumps is the injection of physiologically active fluid into a patient and/or the extraction of body fluid for diagnostic purposes. For this use the pumps are usually equipped with both a contact surface for attaching to a patient's skin and a cannula for the access to the patient's tissue or vessels for introducing an injection fluid or the removal of analysis fluid.

Injection devices are widely used in patient care but their size and complexity largely restricts their use to specialized facilities. Recently, ambulatory use of injection devices has been pioneered in diabetes care for the delivery of insulin. To achieve the necessary precision of delivery these injection devices typically use syringe pumps. The size of these devices is considerable, dictated mainly by the extended, longitudinal shape of a filled syringe with the drawn-out piston, and necessitates their wearing attached to e.g. a belt or underwear and they operate with connective barrels to a subcutaneously placed cannula leading to inconveniences and safety problems.

More recently, because of these drawbacks, infusion devices which can be attached directly to the skin, preferably without long barrels connecting to the subcutaneous delivery cannula are being developed. Due to the necessary reduction in size and weight the precise syringe-type pumps with sufficient volume of injection fluid are difficult to use attached directly to the skin. Therefore, alternative pump types with considerable drawbacks in precision and reliability of delivery under the highly variable environmental and physiologic conditions encountered during real-life operation have been incorporated, e.g. delivery from a reservoir with peristaltic pumps, with piston pumps using valves, or by squeezing a flexible container. Syringe pumps for such applications have barrels with a wide diameter in order to avoid an extended longitudinal footprint, but this solution has disadvantages necessitating high driving forces to inject against a considerable tissue back-pressure and most importantly because of the risk of air bubbles entering and occluding the injection cannula due to almost unavoidable relatively large dead-volumes, and unintended, relatively large bolus injections due to stick-slip effects.

An appealing solution to reduce the footprint of syringe-type pumps with appropriately narrow barrels is to use an arcuate barrel as described e.g. by M. P. Loeb and A. M. Olson in U.S. Pat. No. 4,525,164, filed in 1981. In spite of the attractiveness of this concept for precise patch-type infusion pumps, conversion to safe and cost-effective medical products is not evident, due to considerable practical difficulties in manufacturing such toroidal syringe pumps with the necessary performance at adequate costs. Obviously, such products have to use for the production of the arcuate barrel plastics-technologies with inherent significant tolerance margins because of differences in shrinkage. Since e.g. the mandrel of the injection molding tool has to be removed by a rotary motion and differences in shrinkage of the proximal and distal wall of the torus takes place thereafter, the resulting deviation from an ideal circular shape cannot be easily corrected by adapting the tooling accordingly. The almost unavoidable deviation from an ideal circular shape for the manufactured torus and the deformations under high forces necessary to overcome high tissue back-pressure leads to problems in achieving a sufficient sealing with the piston at reasonable friction and avoiding sticking due to the not perfect fit between the arc of the barrel and the rotary movement of the rigid arcuate driving rod of the piston. These difficulties get even more pronounced at low barrel diameters required for precise syringe-type pumps e.g. for insulin delivery. Despite several more recent descriptions of arcuate syringe pumps, e.g. by R. Paul Mounce et al. in WO 2008/024812 A2 or by O. Yodfad et al. WO 2008/139458 A2 this problem has not been adequately addressed and no practical solutions are obvious from the descriptions or figures.

The aim of the present invention is to provide an arcuate syringe type pump which avoids the disadvantages of the state of the art devices.

SUMMARY OF THE INVENTION

According to the invention this is achieved by the characterizing features of claim 1.

The configuration using a curved toroidal barrel combines the high precision of syringe pumps with a compact shape. In order to achieve an optimal fit between barrel and piston throughout its entire move along the axis of the barrel the driving rod of the piston is guided and supported by the surface of the inner barrel wall and is preferably flexible and thus self-adapting to the inner curvature of the barrel. The barrel has a curvature preferentially with an arc below 180.degree., 150.degree.-160.degree. being most preferred for an optimal length/diameter ratio of the barrel for precision of dosing and which can be manufactured by standard plastics-technologies. Further, with improved individual components of the device and the co-operation of the components a desired reduction in overall size and simplification of mechanical operation is achieved. According to the invention, major problems with current devices are solved by an injection or analysis fluid removal device having the features disclosed herein below.

The subject injection device for introducing an injection fluid into a patient through the patient's skin or through an intravenous or intraperitoneal port comprises a syringe-type pump with a barrel in form of a segment of a toroidal tube and a piston fitting tightly into the barrel which can be passed through the entire barrel actuated by drive and control means. The piston is moved by a driving rod which is guided and supported by the inner wall of the barrel and is preferably flexible and by this self-adapts to the curvature of the barrel without the danger of sticking due to non-perfect fit between the arc of the barrel and the arc of a stiff driving rod of the piston. In addition, this configuration is adaptable to both, delivery of fluid with the rod pushing the piston, being guided by the distal inner surface of the barrel and to withdrawal of fluid with the rod pulling the piston, being guided by the proximal inner surface of the barrel. The device has a contact surface for contacting a patient's skin or an intravenous port. Typically, the contact surface to the skin is coated with an adhesive and the syringe pump is linked to a cannula having a tip which is configured and dimensioned for piercing the patient's skin or a septum of a port and introducing an injection fluid into the patient or removing analysis fluid.

In preferred embodiments, the inventive device has a cannula which is fixedly positioned relative to a casing and to the syringe pump. The insertion mechanism of the cannula into the patient's skin comprises preferably a flexible contact surface adhering to the skin.

When used herein, the following definitions define the stated term

Adhesive contact surface for temporary wearing on the skin is made of materials with strong adhesive properties, stretchability and minimal allergenicity. This adhesive layer is fixed on the base of the device either covering the entire surface or at least its central part leaving a free rim in such a way that it does not interfere with its flexibility. Preferentially the surface of the adhesive layer which is fixed to the skin is significantly larger than its surface which is fixed to the flexible base of the device, leaving a rim which is not fixed to the flexible base. This can be accomplished e.g. by an adhesive layer extending beyond the surface of the base of the device or, preferentially by using a shape for the adhesive surface to the skin similar to or only slightly larger than the surface of the flexible surface of the device but fixing it to the latter in such a way that an outer annular zone is not fixed to the base of the device. Such a design is described in EP0825882 for a medical device with a rigid base.

Analysis fluid is blood, interstitial fluid or dialysate having been in contact with interstitial fluid through a semipermeable membrane.

Analyte means any endogenous or exogenous substance the concentration of which can be used to diagnose the health, organ function, metabolic status, or drug metabolizing capacity of an individual. Examples of endogenous substances are glucose, lactate, oxygen, creatinine, etc. Examples of exogenous substances are drugs, metabolites of such drugs, diagnostic substances (e.g. inulin) etc.

Component with a flexible surface is made up of a casing which has preferentially a circular or oval footprint and which has a flexible base. This base plate is constructed in such a way that it can be deformed to a convex shape with a protruding part e.g. like a cone or a gable (position 1). An additional feature of this base is that it can shoot from the convex shape into a flat shape (position 2) with sufficient velocity and force that this movement can provide the driving energy for implantation of the implantable parts of injection cannulas or diagnostic probes by pulling the skin attached by the adhesive surface against the tip of the cannulas or diagnostic probes. Such a flexible surface can be achieved by appropriate segmentation of the surface with hinge regions acting as springs and/or by using elastic materials with the necessary reversible stretching characteristics which moves e.g. from a pre-stressed shape to adopt a flat, relaxed shape.

Means to position the flexible surface relative to the implantable parts of injection cannulas or diagnostic probes in two defined positions consists of elements which can bring about the deformation of the flexible surface to a convex, pre-stressed shape and allow a rapid release from this position to adopt a flat, relaxed shape in a coordinated way for the entire surface. This can be accomplished preferentially by several pin-shaped elements protruding from the flexible surface and pushing onto a sliding bolt mechanism, but other constructions using screws, ramps, levers etc. are also possible.

Such a component with a flexible surface can be manufactured by injection molding of suitable plastics but also by using other materials like steel, composite or ceramic materials, etc. The base of this element has an opening in form of a hole or slit, as opening for the implantable parts of injection cannulas or diagnostic probes. The implantable parts of injection cannulas or diagnostic probes are positioned axially to this base in such a way that in position 1 they are entirely covered up, whereas in position 2 they protrude the base.

Delivery of injection fluid encompasses both relatively fast injection (bolus) and relatively slow introduction (also called infusion or instillation) of a liquid into the body.

Diagnostic probe is the functional element for the determination of analyte concentrations and means, but is not restricted to, any analysis fluid removal and online analysis or sampling system. In case of a micro-dialysis system a dialysis membrane forms the interface between the interstitial fluid and a dialysis fluid which is passed at the other side of the membrane. In a preferred embodiment a micro-dialysis probe consists of an outer and an inner barrel, covered at the implantable tip by a dialysis membrane. The inner barrel is connected to the pump which delivers the dialysis fluid and the outer barrel is connected to an analysis or sampling system.

Drive and control means contains all necessary mechanical, electronics and software elements for all necessary functions of the device like, but not limited to, moving the piston of the toroidal syringe pump according to internal or external signals, initiating, controlling and surveying the correct functioning of the device, feeding and controlling the diagnostic elements and transforming sensor signals into analyte measurements, storing, displaying and transmitting analyte measurements online or batch-wise, interacting with external control devices, preferentially wirelessly, and giving warning signals if the device is not functioning properly or if analyte measurements are not within a predefined range.

Driving rod of the piston has a construction providing a sufficient radial and axial flexibility to adapt to the actual curvature and axial position of the toroidal barrel but exerting tangentially sufficient stiffness enabling precise movement of the piston within the barrel. Preferentially, the driving rod is flexible and its given form corresponds closely to the arc of the toroidal barrel and a suitable plastics material is used for manufacturing in order to achieve an almost perfect adaptation to the actual form of the inner surface of the barrel with small radial forces. Adaptation of the driving rod to the actual curvature and axial position of the toroidal barrel avoids the possibility of detrimental blockage due to non-perfect fit between the axes of the barrel and of a stiff driving rod.

The flexible driving rod has typically a contact brace allowing low-friction contact with the inner surface of the barrel wall in its median plane and a toothed rack engaging with a cogwheel of the drive means. Low-friction contact between the brace and the inner surface of the barrel wall is achieved by a suitable form and material.

The brace can be an integral part of the driving rod or be attached to it allowing the use of a different material with improved sliding properties and in order to achieve the necessary radial and axial flexibility of the driving rod, the brace can e.g. have a segmented structure.

Another preferred construction replaces sliding contact by a rolling contact to the inner surface of the barrel wall. Such a construction can have e.g. a number of rolls connected by segments having sufficient flexibility at the hinge regions carrying the axes of the rolls to adapt to the curvature of the barrel.

The contact brace absorbs all radial force-components protecting the piston sealing from these forces which can lead to substantial sealing deformation resulting in problems with tightness and stick-slip phenomena up to piston blockage due to non-perfect fit between the axes of the barrel and of a stiff driving rod.

Typically at one end of the driving rod an end-piece in the form of the barrel's cross-section but with slightly smaller diameter is rigidly attached forming a face orthogonally centered relative to the barrel's cross-section by the brace, and transmitting the driving force from the driving rod to the piston sealing tangentially to the axis of the barrel. The piston with its sealing, e.g. an O- or an X-ring is fused with this end-piece or attached to it movably allowing central self-positioning of the piston within the barrel. This can be achieved by a low-friction sliding surface between the end-piece of the driving rod and the piston or by balls rolling at the interface and attenuates possible problems arising from changes in the inner diameter of the barrel along its axis.

Functional package is designed to hold the rigid part of the device by a releasable coupling mechanism and has a removable cap to protect the active surface of the diagnostic probes during storage in a defined environment, such as humidity and allows maintaining sterility. The functional package has also a rim element allowing, after removal of the cap, the correct attachment of the rim of the adhesive layer by pressing against the skin. Further, the functional package protects the release/start mechanism of the device against premature, unintended operation and the release/start mechanism can be actuated only following attachment of the device to the skin and removal of the functional package.

Intravenous port comprises a catheter placed into a vein and having a connective element, preferably a septum at the exterior end of the catheter.

Sampling means is the functional element for collecting samples of analysis fluid for determination of analytes external to the device by, but not limited to biochemical, immunological, HPLC, or LC/MS/MS methods. The samples can be collected in separated receptacles or in a continuous cavity, e.g. a barrel or tube taking precautions, that mixing of samples taken at different times is reduced to a minimum. This can be achieved e.g. by introduction of segments of air or of a non-miscible fluid into the analysis fluid creating separated samples in the continuous cavity.

Sliding bolt mechanisms adapts upon a circular or linear movement consecutively several fixed positions and consists of elements which display a closed or open state, for example a solid surface or a hole. The movement of the slide mechanism is driven manually or for example by a spring actuated by a release element, for example through pressing or releasing a button or handle, or through a turning movement. For inserting in parallel a fluid delivery cannula and a flexible sensor within a guide needle into the skin by means of a component with a flexible surface attached to the skin, movement of the sliding bolt mechanism from the storage position (position 1) to the next position (position 2) upon an easy manipulation actuates a rapid release of the flexible surface from a pre-stressed shape to adopt a flat, relaxed shape and inserts the fluid delivery cannula and sensor guide needle into the skin. The interim blockage of the sliding bolt mechanism at position 2 is now released and allows to actuate the movement of the sliding bolt mechanism to the next position (position 3), which actuates the partial retraction of the guide needle.

DESCRIPTION OF THE DRAWINGS

In the following preferred embodiments of the invention are described with reference to the accompanying drawings in which

FIG. 3 is a diagrammatic cross sectional view of a syringe filling and an injection cannula insertion mechanism into the skin according to one embodiment of the invention.

DESCRIPTION OF THE INVENTION

Figure 1:
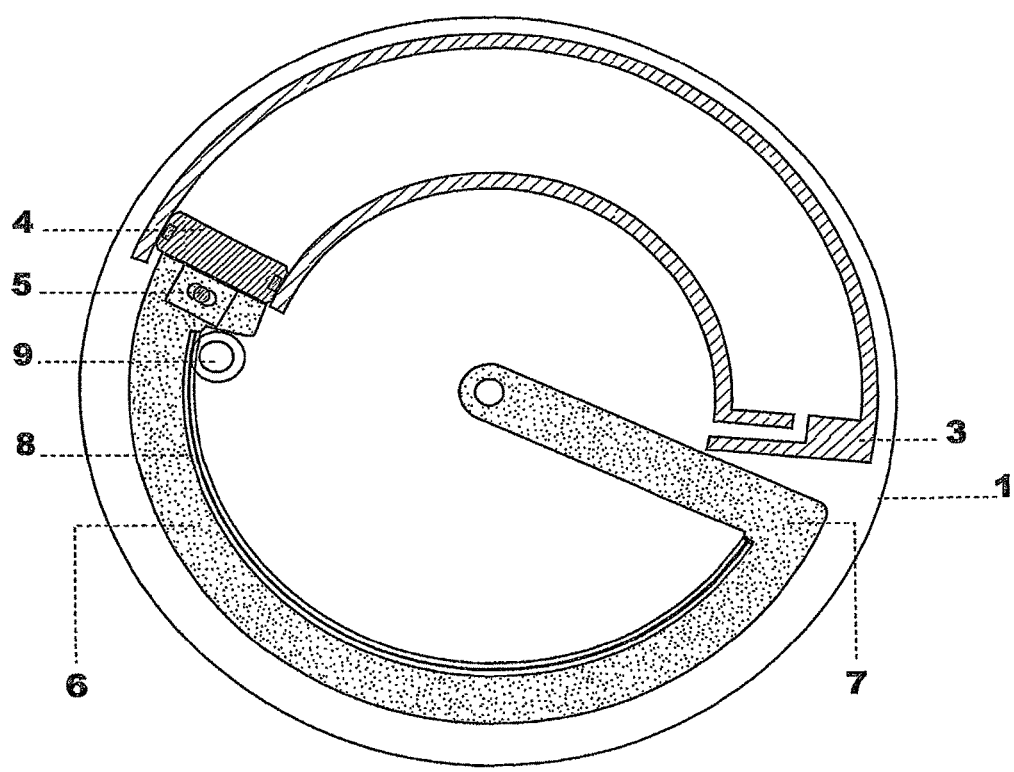
FIG. 1 is a diagrammatic sectional top view of an injection device with a circular syringe pump showing the principle of a circular syringe pump according to state of the art construction but with an improved solution allowing a limited adaptation of the piston to the curvature of the barrel.

The injection device shown in FIG. 1 has a casing having a cylindrical side-wall 1 housing a barrel in form of a segment of a toroidal tube 2. One end 3 of the barrel is provided with a connecting channel to a cannula (not shown). The barrel has a circular cross section.

A piston 4 is arranged in the interior of the barrel and is provided with a seal fitting tightly at the inner wall of the barrel. The piston is connected to a driving rod 6 which is circularly shaped for driving the piston through the entire length of the barrel.

Using established technologies for manufacturing of a toroidal cylinder the fit between its curvature and the driving rod of the piston will not be perfect. To correct for this the mechanism 5 disclosed here connecting the piston to the rod 6 allowing radial adaptation of the piston represents an improvement as compared to the state of the art solutions e.g. as described by M. P. Loeb and A. M. Olson in U.S. Pat. No. 4,525,164, using a resilient spherical piston which is slidably contacted by a cupped distal end of a driving stem allowing it to rotate within the barrel, since such a construction has intrinsic problems of sealing and friction.

At its end opposite the piston the driving rod has a perpendicularly bent arm 7 extending to a central pivot, thereby reducing the radial component of the force and the resulting friction by moving the piston through the barrel. The inner side of the rod has a gear rim 8 which is driven by a gear drive 9. The gear drive is driven e.g. by a gear train and an electrical motor (for example a watchwork drive) which can be regulated for controlled delivery by signals from inbuilt and/or remote control elements (not shown in the figure). Alternatively, other drives, as known in prior art, can be employed.

Using standard manufacturing technologies for the toroidal barrel such as e.g. plastics-technologies with an injection molding tool having a mandrel which has to be removed by a rotary motion, deviations from a perfect circular shape and variations in its shape are unavoidable due to inherent differences in shrinkage e.g. of the proximal and distal part of the torus wall during manufacturing. Because of this almost unavoidable deviation from an ideal circular shape for the manufactured torus the exact geometric fit between the barrel and the driving rod of the piston moved by a rotary motion can not be secured. Even if the driving rod of the piston is manufactured using steel-technologies with a high level of form-stability, the fit of the attached piston to the barrel's shape along its longitudinal axis becomes variable. Indeed, e.g. a difference of only 2% between the radius of the barrel and of the driving rod causes a serious relative shift which can lead to collision between barrel wall and driving rod for torus arcs of e.g. 150.degree.-160.degree. which can be manufactured with standard technologies and are aimed at in order to sufficiently reduce the footprint of the syringe-type pump. In addition, the plastics parts usually used to manufacture the housing holding the barrel and the guideways for the driving rod are not absolutely rigid and can slightly deform especially under the applied forces necessary to provide the pressures of several bar to overcome tissue resistance. The resulting radial and axial forces to correct for the actual shape differences between axis of barrel and driving rod can become very substantial with a rigid driving rod which is used for arcuate piston-drive mechanisms described so far. These forces have to be absorbed by the sealing of the piston leading to its deformation causing high friction with resulting stick-slip phenomena up to blockage and/or problems with tightness of the piston. Even if the piston can adapt slightly to correct for the deviation between the axis of the barrel and of the driving rod as described in prior art and with the improvement discussed and exemplified in FIG. 1 the worst case scenario of blockage by clamping between the rigid driving rod and the barrel wall cannot be excluded. Therefore, for medical use of controlled and precise fluid delivery constructions according to prior art in which a driving mechanism with a rigid driving rod is used to move the piston in an arcuate barrel are not sufficiently safe. These problems get even more pronounced at low barrel diameters required for syringe-type pumps intended for the precise delivery of small volumes such as e.g. insulin for diabetic patients.

According to the subject invention, the solution to avoid stick-slip phenomena and/or problems with tightness or even blockage of the piston or clamping between the rigid driving rod and the barrel wall is to use a driving rod of the piston which adapts to the actual curvature of the barrel, being guided and supported by the inner wall of the barrel. In contrast to constructions described in prior art the rod guided and supported by the inner wall of the barrel of the subject invention can adapt to all deviations from the ideal shape and geometry which are unavoidable using cost-effective manufacturing technologies and materials. A preferred embodiment of the subject invention, which can be adapted for both, fluid delivery and fluid withdrawal, is exemplified in FIG. 2.

Figure 2:
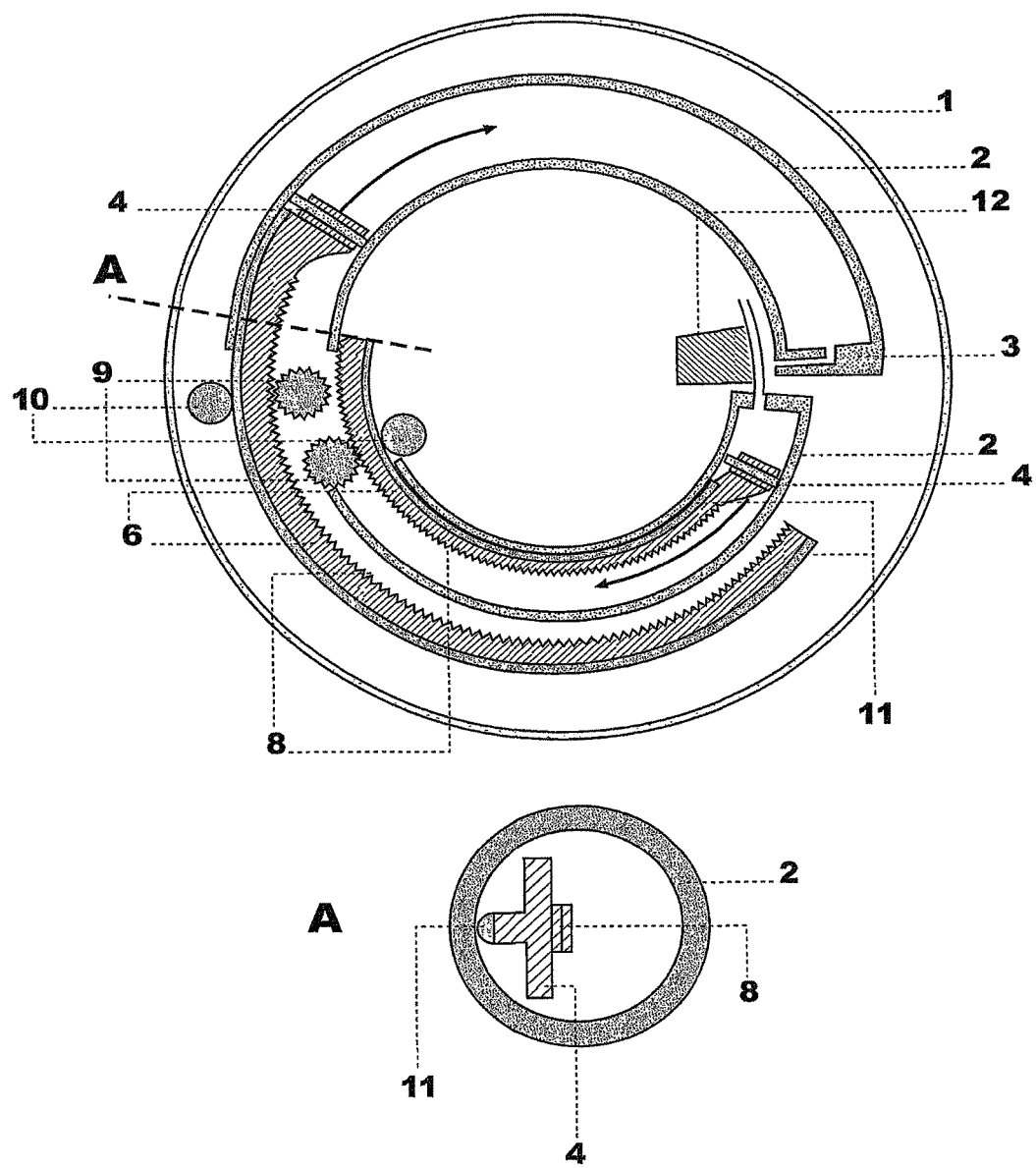
FIG. 2 is a diagrammatic sectional top view of a combined injection and analysis fluid removal device with two circular syringe pumps according to an embodiment of the invention.

FIG. 2 shows a combined injection and analysis fluid removal device with two independent circular syringe pumps in top view of a horizontal section. The pump for delivery of injection fluid is shown in the more peripheral part of the drawing, whereas in the more central part a pump for removal of analysis fluid is shown. In FIG. 2 parts corresponding to FIG. 1 are given the same reference numbers. The embodiment in FIG. 2 does not have a rigid driving rod. Instead, the driving rod 6 of the piston is formed in such a way that its movement is guided and supported by the inner surface of the barrel wall as shown in cross section in Detail A. Importantly, a brace 11 of optimized form and material for even movement with low friction to increase precision and to reduce the necessary forces for piston movement forms the gliding zone between driving rod of the piston and inner surface of the barrel wall. This can be achieved by using for the driving rod plastics with suitable gliding properties or by attaching a rim of suitable material, e.g. a steel wire, but other possibilities of friction reduction like e.g. a construction with a number of rolls the axis of which is held by the brace can be implemented in order to avoid gliding resistance and replace it by rolling resistance.

The radial and axial flexibility of the driving rod exemplified in Detail A can be further increased e.g. by using a segmented structure of the brace holding glidingly a steel wire or the rolls or even a back-bone like structure of the flexible driving rod with segments linked by hinge regions. To ensure safe transmission of the power to the gear rim 8 to move the piston, the gear drive 9 is supported by a radially opposing brace 10, preferentially in the form of an antifriction bearing, pressing against the contact rim 11 of the driving rod, but other constructions like e.g. a side-wall attached to the housing are also possible.

The piston 4 with its sealing, e.g. an O- or an X-ring is held in a defined distance from the inner surface of the barrel wall by the brace of the driving rod and transmits only the tangential driving force to the piston. In addition, to allow self-centering of the piston in the lumen of the barrel, in an alternative construction the piston is not directly fused rigidly with the end of the driving rod, but movably attached to an end-piece of the driving rod which is held by the brace in a defined distance from the barrel wall. This can be achieved e.g. by a low-friction sliding surface contact between the end-piece of the driving rod and the piston or by balls rolling at the interface. Such a self-centering construction might be useful to improve the performance of the pump in case of significant manufacturing process derived variability in the inner shape and diameter of the barrel along its axis.

For delivery of injection fluid the driving rod of the piston is pushing, while guided and supported by the distal inner surface of the barrel (shown in Detail A). In contrast, the circular syringe pump for removal of analysis fluid is operated in suction mode and the driving rod of the piston is pulling, guided and supported by the proximal inner surface of the barrel (mirror image of Detail A, not shown as detail). A proximally located gear rim 8 to move the piston can also be used e.g. in a construction in which the gear rim is double-tracked and set back respective to the brace 11 and the gear drive 9 has a slit to accommodate the protruding brace.

FIG. 3 is the central part of a tangential cut of the device through the end portion 3 of the barrel. A first channel 15 is leading to the upper side of the device and is closed by a septum 14. For filling the barrel with injection fluid a syringe (not shown) having a needle 13 is pierced through the septum 14. Before filling, the piston is touching the end portion 3 of the barrel (not shown). The injection fluid is introduced through channel 15, thereby pushing the piston towards the opposite end of the barrel.

A second channel 17 is leading from the interior of barrel 2 to an injection cannula 16 for delivery of injection fluid into the skin. The cannula 16 is closed at the other end with a septum-seal 18 which is held in a housing 19. The overall construction is such that the dead volume is minimal and no significant volume of air is in the system after filling with injection fluid.

In the exemplified embodiment the insertion means into the skin of the cannula 16 has a flexible base plate 20 which is attached to the skin by an adhesive layer 21. In the ready-to-use mode shown in the figure this flexible base plate is deformed to a convex shape covering the cannula 16. The base plate is preferentially annular or oval and in order to insert a cannula which is remote from the center of the device consists preferentially of two segments with a diagonal slit, forming a gable upon bending. This configuration allows also to use this insertion means for more than one cannula simultaneously which are positioned along the diagonal slit, e.g. if more than one infusion pumps for more than one infusion fluid is used and/or for the combination with insertion of a diagnostic probe into the skin. By the spring-type mechanism, in addition the septum-seal 18 is pierced by the cannula before it enters the skin. The segments are attached to the circumference of the casing 1 by springy hinge regions and are in addition preferentially made of a flexible material. Alternative forms like a radial segmentation, preferably into 5 to 8 segments with a spacing between them and a central opening, forming a cone upon central bending are also possible if the cannula is placed close to the center of the device.

On its underside, the flexible base plate has an annular or oval adhesive layer for securing the device to the patient's skin with a diagonal slit or a concentric central opening, respectively similar to the base plate. This adhesive layer is composed of three parts, a glue for fixing to the flexible base plate, a textile providing the necessary flexibility and a glue for fixing onto the skin. Suitable materials with low allergenicity potential are commercially available. The adhesive layer can have a larger circumference than the device but it could have also the same circumference if the attachment to the base plate leaves an outer zone where it is not connected to the housing.

Upon release of the pre-stressed base plate actuated e.g. by a sliding bolt mechanism (not shown) it rapidly relaxes to a flat shape towards the bottom of the housing of the device 1, pushes the housing 19 of the septum-seal 18, and the cannula 16 pierces through the septum-seal 18 and through the skin attached by the adhesive layer.

Upon reading this specification, various alternative embodiments will become obvious to the skilled artisan. For example, the drive means for moving the piston or the implantation mechanism of the cannula for delivery of injection fluid into a patient, or for removal of analysis fluid of a patient could be achieved via numerous chemical, mechanical, or electrical means. Further, a large variety of diagnostic elements for the online analysis or for sampling of analysis fluid for removed analysis as well as control and measuring means can be accommodated with the device.

The major advantages of a device with a toroidal syringe-type pump described above are its reduced footprint-size by which it can be comfortably worn and operated by the patient and at the same time the inherent high precision of a syringe type pump. The intrinsic problems of such pumps exemplified in prior art of sealing, friction causing stick-slip phenomena, and even blockage caused by lack of exact fit between the actual form of the arcuate barrel and of the plunger unavoidable in manufacturing of the toroidal barrel and the device using standard cost-effective technologies are solved by using as the drive for the piston a driving rod which is guided and supported by the inner wall of the barrel and therefore can adapt to all deviations from the ideal shape and in geometry. A further advantage is the absence of the problems with connecting tubings between a syringe pump and the cannula penetrating the skin. In addition, the device according to the invention has almost no dead volume thus avoiding complicated mechanisms to move air out of the system during filling of the pump with injection fluid.

We claim:

1. A device for subcutaneous injection of fluid into a patient's skin, comprising:
    a casing to house a pump;
    a cannula having a tip for insertion into the patient's skin, the cannula being fixed in a position relative to the pump;
    a flexible base plate, the base plate fixed to the casing and including (1) a pre-stressed convex position in which the tip of the cannula is concealed, and (2) a released flat position in which the tip of the cannula is exposed beyond the base plate; and
    an adhesive layer fixed to a central region of the flexible base plate and extending without interruption towards an outer portion of the flexible base plate to adhere the base plate onto the patient's skin,
    wherein when moving from the pre-stressed convex position to the released flat position, a portion of the base plate which is moving pulls the skin which is adhered to the base plate so that the patient's skin moves against and is pierced by the tip of the cannula,
    wherein when the device is in (1) the pre-stressed convex position, a tip of the cannula is contained within the device,
    wherein when the device is in (2) the released flat position, the tip of the cannula is exposed beyond the baseplate, and
    wherein as the device transitions from (1) the pre-stressed convex position to (2) the released flat position, the cannula moves from being contained within the device to being exposed beyond the base plate such that a tip of the cannula is outside of the device.

2. The device according to claim 1 wherein the pump is a circular syringe pump.

3. The device according to claim 1 wherein the device includes more than one cannula for insertion into the skin simultaneously by a single cannula insertor.

4. The device according to claim 1 further comprising:
    a cannula insertor, the cannula insertor actuates the piercing of a septum before insertion into the skin.

5. The device according to claim 1 wherein the device comprises more than one pump for delivery of injection fluid into the patient.

6. The device according to claim 1 wherein the adhesive layer is temporarily worn by the patient.

7. The device according to claim 6 wherein a surface of the flexible base plate is smaller than a surface of the adhesive layer.

8. The device according to claim 1 wherein the flexible base plate is elastic for rapid movement between the pre-stressed convex position and the released flat position.

9. The device according to claim 1 wherein the device is applied to the skin using a functional package with a rim pressing the adhesive layer towards the skin.

* * * * *